United States Patent [19]

Durairaj

[11] Patent Number: 5,300,618

[45] Date of Patent: Apr. 5, 1994

[54] RESORCINOL-BASED EPOXY RESINS

[75] Inventor: Raj B. Durairaj, Monroeville, Pa.

[73] Assignee: Indspec Chemical Corporation, Pittsburgh, Pa.

[21] Appl. No.: 3,987

[22] Filed: Jan. 15, 1993

[51] Int. Cl.$^5$ .................. C07D 303/12; C07D 303/34
[52] U.S. Cl. ..................................... 528/101; 528/87; 528/91; 528/93; 528/94; 528/98; 528/109; 528/124; 549/556
[58] Field of Search ................ 549/556; 528/98, 87, 528/101

[56] References Cited

U.S. PATENT DOCUMENTS

| | | | |
|---|---|---|---|
| 2,467,171 | 4/1944 | Werner et al. | 260/348 |
| 2,892,849 | 6/1959 | St. Clair | 260/348.6 |
| 3,291,837 | 12/1966 | Goldberg et al. | 260/591 |
| 4,656,207 | 4/1987 | Jabloner et al. | 523/400 |
| 4,916,202 | 4/1990 | Butler et al. | 528/98 |

FOREIGN PATENT DOCUMENTS 61-186375 2/1985 Japan.
61-186376 2/1985 Japan.

OTHER PUBLICATIONS

Chemical Abstract 107(20):176973m, "Development of Heat Resistant Epoxy Resins".
Chemical Abstract 104(18):1500486, "Epoxy Resin Compositions for Carbon Fiber Reinforcement".
"Epoxy Resins from Resorcinol—Acetone Condensation Products", Industrial and Engineering Chemistry, vol. 52, No. 4, Apr. 1960 pp. 324–325.

*Primary Examiner*—Frederick Krass
*Attorney, Agent, or Firm*—Arnold B. Silverman; Jolene W. Appleman

[57] ABSTRACT

A curable resorcinol-based epoxy resin is disclosed having the general structural formula (I)

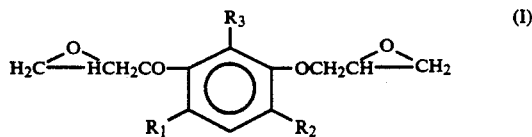

wherein at least one of $R_1$, $R_2$, or $R_3$ is selected from the group consisting of (a) the general structural formula (II)

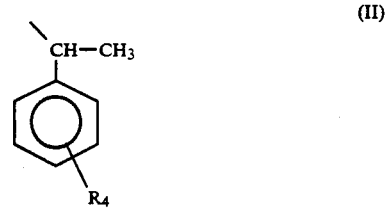

wherein $R_4$ is selected from the group consisting of hydrogen and an alkyl group having 1 to about 4 carbon atoms, and (b) an allyl group.

3 Claims, No Drawings

RESORCINOL-BASED EPOXY RESINS

BACKGROUND OF THE INVENTION

1. Field of the Invention

This invention relates to resorcinol-based epoxy resins having improved physical and mechanical properties such as a reduced ability to absorb moisture, high glass transition temperature, good processability and less volatility.

2. Brief Description of the Prior Art

Epoxy resins are a class of thermoset resins with a wide range of applications. For example, epoxy resins are employed in composite fabrication in both wet and dry lay-up techniques well known to those skilled in the art for the electrical, aerospace, filament winding and hardware industries. The disadvantage of many epoxy resins is their ability to absorb high amounts of moisture when they are used in both wet and dry composite fabrication. Obtaining an epoxy resin having a low moisture absorption characteristic, however, in many cases, has led to a compromise in other desirable physical and mechanical properties such as, for example, high glass transition temperature, ease of processability, flexural properties, tensile properties and curing conditions.

It is well known that all epoxy resins contain the epoxide, orirane or ethoxylene group:

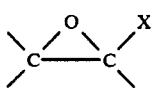

wherein X represents the point of attachment to the remainder of the resin molecule. The epoxide function generally appears in the form:

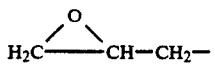

known by those skilled in the art as the glycidyl group which is attached to the remainder of a compound by such as, for example, an oxygen (i.e., glycidyl ether), nitrogen (i.e., glycidyl amine), or carboxyl group (i.e., glycidyl ester).

U.S. Pat. No. 2,892,849 discloses a process for preparing epoxyalkyl aryl ethers, including resorcinol diglycidyl ether.

U.S. Pat. No. 4,916,202 discloses an epoxy resin having glycidyl amine groups. This patent discloses epoxy resins made from aliphatic amines, sulfonamides, and aromatic amines.

Japanese Patent No. -026173 discloses a process for making an epoxy resin from a carboxylic acid derivative of resorcinol such as Beta-resorcylic acid.

Japanese Patent No. -020172 discloses the process of making an epoxy resin from the reaction of another resorcinol derivative namely 4,4'-thiodiresorcinol with the epichlorohydrin.

U.S. Pat. No. 2,467,171 discloses stereoisomeric 1,3-diglycidyloxybenzenes which have been known for many years.

*Industrial and Engineering Chemistry*, Volume 52, No. 4, Apr. 1960, pp. 324-325 discloses epoxy resins from resorcinol-acetone condensation products.

U.S. Pat. No. 3,291,837 discloses the preparation of monoepoxy compounds from benzyol resorcinol and thier application towards U.V. stabilizers.

U.S. Pat. No. 4,656,207 discloses resorcinol-based epoxy compounds but not benzoyl resorcinol diglycidyl ether compounds.

None of the prior art discloses the preparation and application of diglycidyl ether derivatives of benzyol resorcinol, styryl- and alphamethyl styryl substituted resorcinol and also the tetraglycidyl ether of bis[resorcinol] type resin of the present invention.

In spite of these prior art disclosures, there remains a very real and substantial need for a resorcinol-based epoxy resin having enhanced curing properties, flexural properties, tensile properties, low moisture absorption properties, a high glass transition temperature and less volatility.

SUMMARY OF THE INVENTION

The present invention has met the above-described need. The present invention provides a resorcinol-based curable epoxy resin having the general structural formula (I)

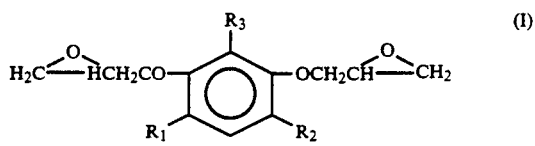

wherein at least one of $R_1$, $R_2$, or $R_3$ is selected from the group consisting of (a) the general structural formula (II)

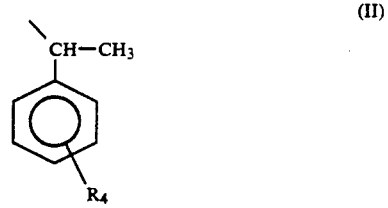

wherein $R_4$ is selected from the group consisting of hydrogen and an alkyl group having 1 to about 4 carbon atoms, and (b) an allyl group.

In another embodiment of this invention, a curable epoxy resin is provided having the general structural formula (III)

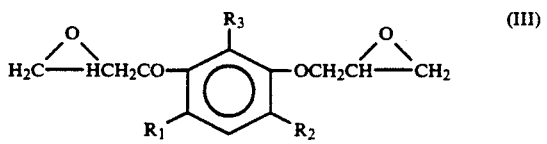

wherein at least one of $R_1$, $R_2$, or $R_3$ is selected from the group consisting of (a) the general structural formula (IV)

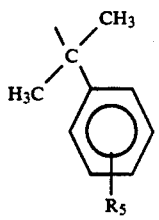
(IV)

wherein $R_5$ is selected from the group consisting of hydrogen and an alkyl group having 1 to about 4 carbon atoms, and (b) an allyl group.

In another embodiment of this invention, a curable epoxy resin is provided having the general structural formula (V)

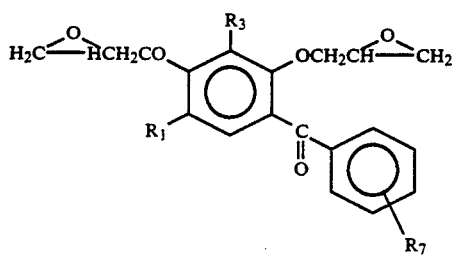
(V)

wherein $R_1$ and $R_3$ may be the same or different and selected from the group consisting of (a) hydrogen, (b) the general structural formula (VI)

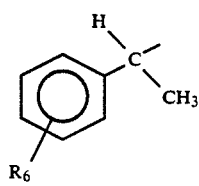
(VI)

and (c) an allyl group, and wherein $R_6$ and $R_7$ may be the same or different and selected from the group consisting of hydrogen and an alkyl group having 1 to about 4 carbon atoms.

In a preferred embodiment of this invention, a curable epoxy resin is provided having the general structural formula (VII)

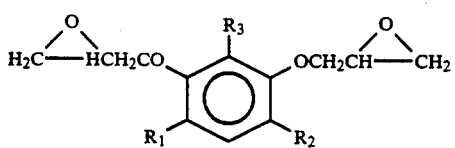
(VII)

wherein $R_3$ is hydrogen, and wherein $R_1$ is selected from the group consisting of (a) the general structural formula (VIII)

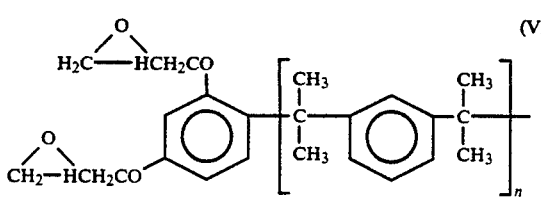
(VIII)

when $R_2$ is hydrogen and wherein n is the integer 1, and (b) hydrogen when $R_2$ is the general structural formula (IX)

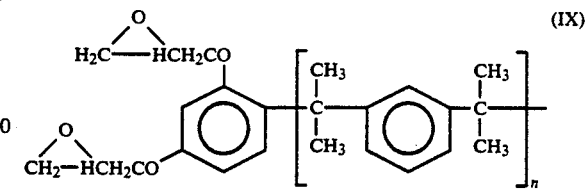
(IX)

and wherein n is the integer 1.

Yet another embodiment of this invention provides a curable epoxy resin having the general structural formula (X)

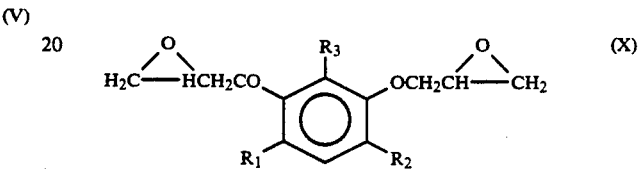
(X)

wherein $R_3$ is hydrogen, and wherein $R_1$ is selected from the group consisting of (a) a compound having the general structural formula (XI)

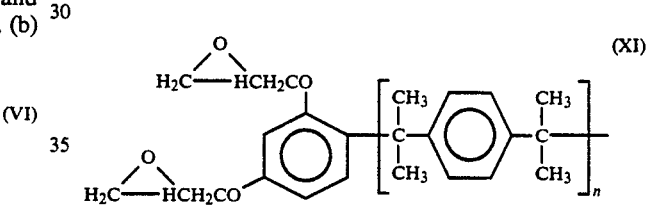
(XI)

when $R_2$ is hydrogen and wherein n is the integer 1, and (b) hydrogen when $R_2$ is a compound having the general structural formula (XII)

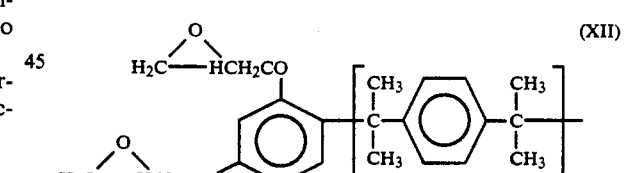
(XII)

and wherein n is the integer 1.

In another embodiment of this invention, a chemical composition is provided having the general structural formula (XIII)

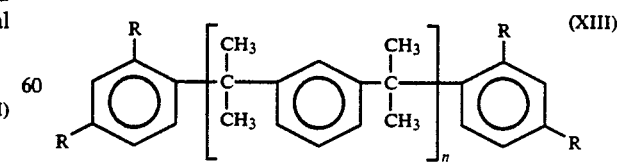
(XIII)

wherein R is —OH and n is the integer 1.

Yet another embodiment of this invention provides for a chemical composition having the general structural formula (XIV)

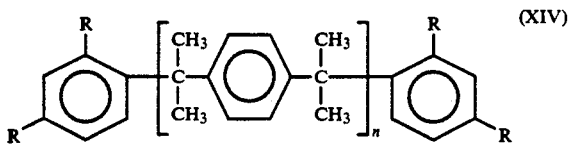

wherein R is —OH and n is the integer 1.

It is an object of the present invention to provide a curable, resorcinol-based epoxy resin having improved physical and mechanical properties including a substantially high glass transition temperature, a reduced moisture absorption capability, enhanced flexural and tensile properties, and a substantially low viscosity.

It is another object of this invention to provide a resorcinol-based epoxy resin that may be cured with conventional curing agents.

It is another object of this invention, in view of the present environmental concerns of society, to make a less volatile resorcinol-based epoxy resin compound that is characterized as nontoxic compared with other known resorcinol epoxy resins.

These and other objects of the invention will be more fully understood from the following description of the invention and the claims appended hereto.

DESCRIPTION OF THE PREFERRED EMBODIMENTS

The present invention is directed to improvements in the physical and mechanical properties such as, for example, the moisture absorption capability, glass transition temperature, flexural and tensile properties, volatility, and the viscosity of curable resorcinol-based epoxy resins.

As used herein, the term "allyl" means the allyl system including, but not limited to, allyl cations, allyl free radicals and allyl anions.

The curable epoxy resin of this invention has the following general structural formula (I)

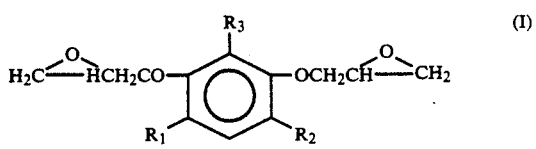

wherein at least one of $R_1$, $R_2$ or $R_3$ is selected from the group consisting of (a) the general structural formula (II)

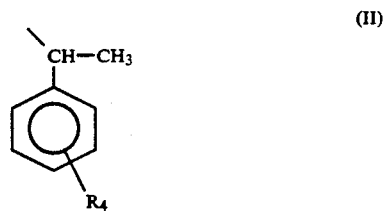

wherein $R_4$ is selected from the group consisting of hydrogen and an alkyl group having one to about four carbon atoms, and (b) an allyl group.

In another embodiment of this invention, a curable epoxy resin is provided having the general structural formula (III)

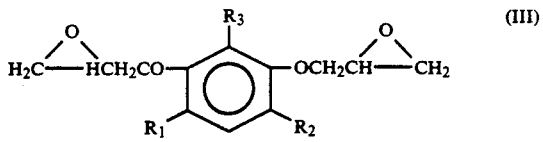

wherein at least one of $R_1$, $R_2$, or $R_3$ is selected from the group consisting of (a) the general structural formula (IV)

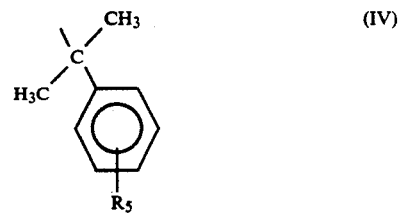

wherein $R_5$ is selected from the group consisting of hydrogen and an alkyl group having one to about four carbon atoms, and (b) an allyl group.

This invention further provides a curable epoxy resin having the general structural formula (V)

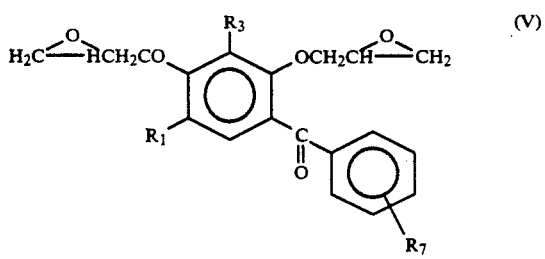

wherein $R_1$ and $R_3$ may be the same or different and selected from the group consisting of (a) hydrogen, (b) the general structural formula (VI)

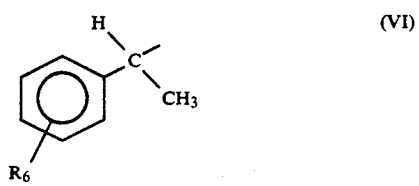

and (c) an allyl group, and wherein $R_6$ and $R_7$ may be the same or different and selected from the group consisting of hydrogen and an alkyl group having one to about four carbon atoms.

In a preferred embodiment of this invention, a curable epoxy resin is provided having the general structural formula (VII)

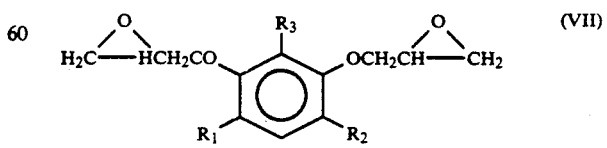

wherein $R_3$ is hydrogen, and wherein $R_1$ is selected from the group consisting of (a) the general structural formula (VIII)

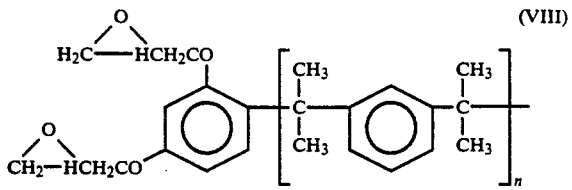

when $R_2$ is hydrogen and wherein n is the integer 1, and (b) hydrogen when $R_2$ is the general structural formula (IX)

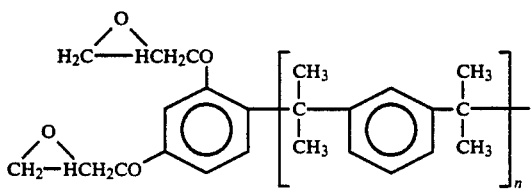

and wherein n is the integer 1.

In another preferred embodiment of this invention, a curable epoxy resin is provided having the general structural formula (X)

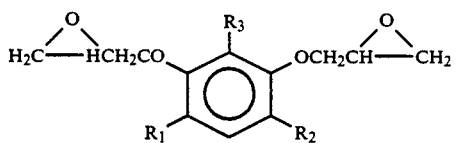

wherein $R_3$ is hydrogen, and wherein $R_1$ is selected from the group consisting of (a) the general structural formula (XI)

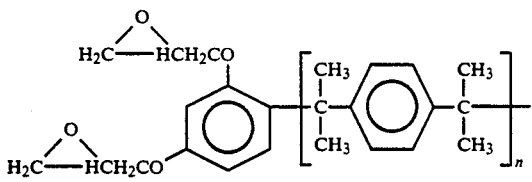

when $R_2$ is hydrogen and wherein n is the integer 1, and (b) hydrogen when $R_2$ is the general structural formula (XII)

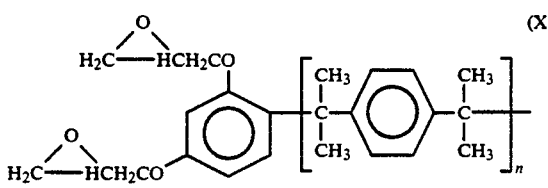

and wherein n is the integer 1.

In yet another embodiment of this invention, a chemical composition is provided having the general structural formula (XIII)

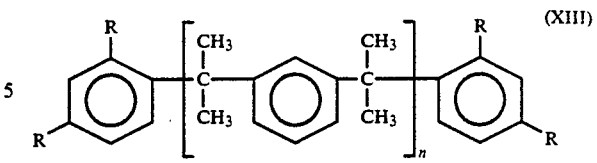

wherein R is —OH, and n is the integer 1.

A further embodiment of this invention provides for a chemical composition having the general structural formula (XIV)

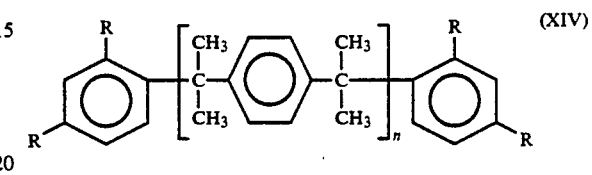

wherein R is —OH and n is the integer 1.

The epoxy resins of formulas (I) through (XII) are readily prepared by synthesis methods known by those skilled in the art. These epoxy resins can be cured in a conventional manner. For example, a suitable curing agent for the epoxy resins of the present invention is 4-diaminodiphenyl sulfone (DDS). It will be appreciated by those skilled in the art that cures normally involve an added accelerator such as, for example, benzyldimethylamine (BDMA) and boron trifluoride in the form of its monoethylamine, piperidiene or methylimidazole complex. The epoxy resins of this invention may also be mixed with conventional epoxy resins prior to curing.

It will be appreciated by those skilled in the art that while each commercially available epoxy resin has a number of advantageous properties, each resin, however, has a shortcoming in that it substantially lacks at least one of the hereinbefore mentioned properties generally required by those skilled in the art. By contrast, the epoxy resins of this invention generally have high glass transition temperatures, low water absorption properties and improved flexural and tensile properties in comparison to the epoxy resin systems currently available. In this regard, the epoxy resins of this invention are well suited for use in the aircraft industry as fiber reinforcements. Laminates made from the epoxy resin matrices of this invention include the use of fibers such as, for example, glass, polyaramid and carbon. It will be understood by those skilled in the art that the epoxy resin composites of this invention may be fabricated using conventional wet lay-up and dry lay-up methods. The reinforced fiber may be impregnated with the epoxy resin matrice to produce a prepeg sheet. The epoxy resins of this invention are also suitable, for example, in the liquid form for filament winding, reaction injection molding, resin transfer molding and pultrusion. The epoxy resins of this invention are less volatile because of their bulky substituents and are therefore nontoxic as compared with other known resorcinol epoxy resins. The present invention is further illustrated by the following examples.

EXAMPLE 1

This example illustrates the preparation of the epoxy resin of this invention having the structure shown in formula (V).

Synthesis of Epoxy Resin from Benzoylresorcinol [DEBR]

Benzoylresorcinol (240.8 grams; 1.125 moles) and epichlorohydrin (1041 grams; 11.25 moles) were placed in a 3-liter round bottomed flask fitted with a stirrer, thermometer, Dean Stark condenser and an addition funnel. The contents of the flask were heated to about 100°–125° Centigrade (C) and an aqueous sodium hydroxide solution (50% W/W; 183 grams; 2.29 moles) was slowly added into the refluxing solution of benzoylresorcinol and the epichlorohydrin. While continuously removing the azeotropic water, the separated epichlorohydrin was continuously returned to the reaction flask. The addition time of sodium hydroxide was between about 1 to 1½ hours and the time required for the complete removal of water (132 grams) was about 2 to 2½ hours. After this, the excess epichlorohydrin was distilled out first under atmospheric pressure and then under vacuum distillation conditions [maximum pot temperature about 130°–135° C. and vacuum about 27–28 inches (") of mercury (Hg)]. Then about 1200 ml of acetone was added to the reaction flask and the contents were refluxed for about 15 minutes to dissolve the epoxide. Finally, the salt, sodium chloride was filtered and the solvent acetone was distilled out using both atmospheric and vacuum distillation conditions (temperature about 95°–97° C. and vacuum about 27–28" of Hg) to obtain 352 grams (yield=96%) of epoxide having an epoxide equivalent weight (EEW) of 180.

EXAMPLE 2

This example illustrates the epoxy resin of this invention having the structural formula (V).

Synthesis of Epoxy Resin from Benzoylresorcinol [DEBR]

Benzoylresorcinol (272.9 grams; 1.275 moles) and epichlorohydrin (1180 grams; 12.75 moles) were placed in a 3-liter round bottomed flask fitted with a stirrer, thermometer, Dean Stark condenser and an additional funnel. The contents of the flask were heated to about 100°–125° C. and an aqueous sodium hydroxide solution (50% W/W; 207.4 grams; 2.59 moles) was slowly added into the refluxing solution of benzoyl-resorcinol and epichlorohydrin. While continuously removing the azeotropic water, the separated epichlorohydrin was continuously returned to the reaction flask. The addition time of sodium hydroxide was between about 1 to 1½ hours and the time required for the complete removal of water (149.6 grams) was about 2 to 2½ hours. After this, the excess epichlorohydrin was distilled out first under atmospheric pressure and then vacuum distillation conditions (maximum pot temperature about 130°–135° C. and vacuum about 27–28" of Hg). Then about 1300 ml of acetone was added to the reaction flask and the contents were refluxed for about 15 minutes to dissolve the epoxide. Finally, the salt, sodium chloride was filtered and the solvent acetone was distilled out using both atmospheric and vacuum distillation conditions (temperature about 95°–97° C. and vacuum about 27–28" of Hg) to obtain 412 grams (yield=99%) of epoxide having an epoxide equivalent weight of 194.

EXAMPLE 3

This example illustrates the preparation of the epoxy resin of this invention having the structural formula (V).

Synthesis of Epoxy Resin of Benzoylresorcinol [DEBR]

Benzoylresorcinol (272.9 grams; 1.275 moles) and epichlorohydrin (1180 grams; 12.75 moles) were placed in a 3-liter round bottomed flask fitted with a stirrer, thermometer, Dean Stark condenser and an addition funnel. The contents of the flask were heated to about 100°–125° C. and an aqueous sodium hydroxide solution (50% W/W; 214.5 grams; 2.68 moles) was slowly added into the refluxing solution of benzoyl-resorcinol and epichlorohydrin. While continuously removing the azeotropic water, the separated epichlorohydrin was continuously returned to the reaction flask. The addition time of sodium hydroxide was between about 1 to 1½ hours and the time required for the complete removal of water (153.2 grams) was about 2 to 2½ hours. After this, the excess epichlorohydrin was distilled out first under atmospheric pressure and then vacuum distillation conditions (maximum pot temperature about 130°–135° C. and vacuum about 27–28" of Hg). Then about 1300 ml of acetone was added to the reaction flask and the contents were refluxed for about 15 minutes to dissolve the epoxide. Finally, the salt, sodium chloride was filtered and the solvent acetone was distilled out using both atmospheric and vacuum distillation conditions (temperature about 95°–97° C. and vacuum about 27–28" of Hg) to obtain 402.5 grams (yield=97%) of epoxide having an epoxide equivalent weight of 195.

EXAMPLE 4

This example illustrates the epoxy resin of this invention having structural formula (I).

Synthesis of Epoxy Resin from Styryl-substituted Resorcinol

Preparation of Styrenated Resorcinol

Into a 1-liter reaction flask equipped with a stirrer, thermometer, reflux condenser and addition funnel, 165.0 grams of resorcinol were charged and heated to about 120°–130° C. para-Toluene sulfonic acid (1.0 gram) was then added at about 120° C. and mixed for about 5 minutes. Then 234.5 grams of styrene (2.25 moles) were slowly added to the molten resorcinol dropwise over a period of about 1½ hours. The temperature of the reaction mixture was maintained between about 115°–135° C. during the styrene addition. After all of the styrene had been added, the reaction mixture was stirred at about 115°–135° C. for about an additional 1 to 1½ hours. At the end of this period 0.5 grams of 50% W/W sodium hydroxide solution was added to neutralize the acid before cooling to room temperature. Structural characterization using infrared spectroscopy (IR) and nuclear magnetic resonance spectroscopy (NMR) of the above reaction product indicated the presence of 1.5 styryl groups per resorcinol molecule. Analysis employing liquid chromatography (LC) and gas chromatography (GC) showed the presence of 1.4 weight percent unreacted resorcinol and also 0.01 weight percent unreacted styrene in the final product.

Preparation of an Epoxy Resin from Styrenated Resorcinol [DGESR]

Styryl resorcinol (359.0 grams; 1.35 moles) and epichlorohydrin (1249 grams; 13.5 moles) were placed in a 5-liter round bottomed flask fitted with a stirrer, thermometer, Dean Stark condenser and an additional funnel. The contents of the flask were heated to about 100°-125° C. and an aqueous sodium hydroxide solution (50% W/W; 226.8 grams; 2.84 moles) was slowly added into the refluxing solution of styryl resorcinol and epichlorohydrin. While continuously removing the azeotropic water, the separated epichlorohydrin was continuously returned to the reaction flask. The addition time of sodium hydroxide was between about 1 to 1½ hours and the time required for the complete removal of water (155 grams) was about 2 to 2½ hours. After this, the excess epichlorohydrin was distilled out first under atmospheric pressure and then vacuum distillation conditions (maximum pot temperature about 130°-135° C. and vacuum about 27-28" of Hg). Then about 1500 ml of acetone was added to the reaction flask and the contents were refluxed for about 15 minutes to dissolve the epoxide. Finally, the salt, sodium chloride was filtered and the solvent acetone was distilled out using both atmospheric and vacuum distillation conditions (temperature about 95°-97° C. and vacuum about 27-28" of Hg) to obtain 514.5 grams of epoxide having an epoxide equivalent weight of 242. Structural characterization by IR/NMR analysis of the epoxide showed 1.83 epoxide groups per molecule.

EXAMPLE 5

This example illustrates the epoxy resin of this invention having the structural formula (I).

Synththesis of Epoxy Resin from Styryl-substituted Resorcinol [DGEBR]

Into a 1-liter reaction kettle fitted with a stirrer, thermometer, Dean Stark reflux condenser and an addition funnel, 33.0 grams of resorcinol (0.3 moles) were placed. The kettle was then heated to melt the solid resorcinol. While maintaining the temperature of molten resorcinol between about 130° and 145° C., the catalyst p-toluenesulfonic acid (0.2 grams) was added first followed by the slow addition of 46.9 grams of styrene (0.45 moles) over a period of about ½ hour. After the styrene addition the reaction mixture was stirred at this temperature for about an additional 1.0 hour. Finally 0.2 grams of sodium hydroxide (50% W/W) was added to neutralize the acid catalyst. The styryl-substituted resorcinol made was cooled to about room temperature before adding 227.5 grams of epichlorohydrin (3.0 moles). The contents of the kettle were again heated to about 100°-125° C. and an aqueous sodium hydroxide solution (50% W/W; 50.4 grams; 0.63 moles) was slowly added into the refluxing solution of styryl resorcinol and epichlorohydrin. While continuously removing the azeotropic water, the separated epichlorohydrin was continuously returned to the reaction flask. The addition time of sodium hydroxide was about 1 to 1½ hours and the time required for the complete removal of water was about 2 to 2½ hours. After this, the excess epichlorohydrin was distilled out first under atmospheric pressure and then vacuum distillation conditions (maximum pot temperature about 130°-135° C. and vacuum about 27-28" of Hg). Then, about 300 ml of acetone was added to the reaction flask and the contents were refluxed for about 15 minutes to dissolve the epoxide. Finally, the salt, sodium chloride was filtered and the solvent acetone was distilled out using both atmospheric and vacuum distillation conditions (temperature about 95°-97° C. and vacuum about 27-28" of Hg) to obtain 104.3 grams of epoxide (yield=92%) having an epoxide equivalent weight of 215. Structural characterization by IR/NMR analysis of the epoxide showed 1.97 epoxide groups per molecule.

EXAMPLE 6

This example illustrates the epoxy resin of this invention having the structural formula (III).

Synthesis of Epoxy Resin from Alpha-Methylstyryl-substituted Resorcinol

Preparation of Alpha-Methylstyryl Resorcinol

Into a 3-liter kettle fitted with a stirrer, thermometer, reflux condenser and an addition funnel 137.5 grams of resorcinol (1.25 moles), 10.0 grams of oxalic acid, 900 ml of heptane were placed. The contents of the flask were then heated to about 65° C. While maintaining the temperature of the resorcinol slurry between about 65° and 75° C., 312 grams of alpha-methyl styrene (2.6 moles) was added dropwise with stirring for about 2.0 hours. After the completion of the above addition, the temperature of the reaction mixture was raised to and maintained at about 95° C. and for an additional period of about 2.0 hours while the reaction mixture was continuously stirred. The reaction mixture was cooled and the colorless product that separated was filtered, washed several times with distilled water and dried in air at about room temperature to obtain 376 grams of alpha-methylstyryl-substituted resorcinol (yield=84%). Structural characterization by IR/NMR analysis of the above reaction product showed the presence of 1.85 alpha-methylstyryl groups per resorcinol molecule.

Preparation of an Epoxy resin from Alpha-Methylstyrenated Resorcinol [DGEMSR]

Alpha-methylstyryl resorcinol (65.6 grams; 0.2 moles) and epichlorohydrin (148 grams; 1.6 moles) were placed in a 500-ml round bottomed flask fitted with a stirrer, thermometer, Dean Stark condenser and an additional funnel. The contents of the flask were heated to about 100°-125° C. and an aqueous sodium hydroxide solution (50% W/W; 36.8 grams; 0.46 moles) was slowly added into the refluxing solution of alpha-methylstyryl resorcinol and epichlorohydrin. While continuously removing the azeotropic water, the separated epichlorohydrin was continuously returned to the reaction flask. The addition time of sodium hydroxide was about 1.0 hour and the time required for the complete removal of water (25.6 grams) was about 1½ to 2 hours. After this, the excess epichlorohydrin was distilled out first under atmospheric pressure and then vacuum distillation conditions (maximum pot temperature about 130°-135° C. and vacuum about 27-28" of Hg). Then about 200 ml of acetone was added to the reaction flask and the contents were refluxed for about 15 minutes to dissolve the epoxide. Finally, the salt, sodium chloride was filtered and the solvent acetone was distilled out using both atmospheric and vacuum distillation conditions (temperature about 95°-97° C. and vacuum about 27-28" of Hg) to obtain 88.0 grams of epoxide having an epoxide equivalent weight of 255. Structural characterization by IR/NMR analysis of the epoxide showed 1.94 epoxide groups per molecule.

EXAMPLE 7

This example illustrates the epoxy resin of this invention having the structural formula (VII).

Synthesis of Epoxy Resin from 1,3-Bis [(2,4-di-hydroxyphenyl)-alpha-methyl ethyl]benzene

Preparation of 1,3-Bis [(2,4-di-hydroxyphenyl)-alpha-methyl ethyl] benzene

Into a 2-liter kettle equipped with stirrer, thermometer, reflux condenser and an addition funnel, 264.0 grams of resorcinol (2.4 moles) 12.0 grams of oxalic acid and 900 ml of heptane were placed. The contents of this flask were heated to about 75° C. While maintaining the temperature of the resorcinolic slurry between about 75°-85° C., 126.4 grams of 1,3-diisopropenyl benzene (0.8 moles) was added dropwise for about 2 hours. After the completion of the above addition, the temperature of the reaction mixture was raised to and maintained at about 95° C. for about an additional 2.0 hours, while the reaction mixture was continuously stirred. The reaction mixture was then cooled and the separated heptane layer was removed by decantation. Finally the solidified mass was treated with excess dichloromethane to separate the reaction product. The white precipitate that separated from the solution was filtered, washed with dichloromethane and then washed with distilled water. After air drying at about room temperature the precipitate weighed 215 grams. Structural characterization by IR/NMR analysis of the reaction product confirmed the structure of 1,3-bis[(2,4-di-hydroxyphenyl)-alpha-methyl ethyl] benzene.

Preparation of an Epoxy Resin from 1,3-Bis [(2,4-di-hydroxyphenyl)-alpha-methyl ethyl benzene 1,3-Bis [(2,4-di-hydroxyphenyl)-alpha-methyl ethyl] benzene (15.1 grams; 0.04 moles) and epichlorohydrin (74.0 grams; 0.8 moles) were placed in a 500 ml round bottomed flask fitted with a stirrer, thermometer, Dean Stark condenser and an addition funnel. The contents of the flask were heated to about 100°-125° C. and an aqueous sodium hydroxide solution (50% W/W; 13.4 grams; 0.168 moles) was added slowly into the refluxing solution. While continuously removing the azeotropic water, the separated epichlorohydrin was continuously returned to the reaction flask. The addition time of sodium hydroxide was about 1.0 hour and the time required for the complete removal of water (9.6 grams) was about 1½ to 2 hours. After this, the excess epichlorohydrin was distilled out first under atmospheric pressure and then vacuum distillation conditions (maximum pot temperature about 140°-150° C. and vacuum about 27-28" of Hg). Then, about 130 ml of acetone was added to the reaction flask and the contents were refluxed for about 15 minutes to dissolve the epoxide. Lastly, sodium chloride was filtered out and the solvent acetone was distilled out using both atmospheric and vacuum distillation conditions (temperature about 95°-97° C. and vacuum about 27-28" of Hg) to obtain 17.4 grams of a light yellow 1,3-bis [(2,4-di-(2,3-epoxypropoxy) phenyl)-alpha-ethylethyl] benzene having an epoxy equivalent weight of 210. Structural characterization by IR/NMR of this epoxide showed 3.76 epoxide groups (Theory=4.0) per molecule. Differential scanning calorimetry (DSC) analysis showed that this resin had a softening point of 59.8° C.

The epoxy resin prepared above was combined with the curing agent 4-diaminodiphenyl sulfone (DDS) in a ratio of 10.0 grams of epoxy resin to 3.0 grams of DDS and cured to prepare a sample for the determination of glass transition temperature (Tg). The cure cycle employed was about 2.0 hours at about 150° C. followed by about 4.0 hours at about 200° C. The thermal mechanical analysis (TMA) measurements made on this cured epoxy resin showed a Tg of 244.7° C. This analysis was carried out in a nitrogen atmosphere at a heating rate of 10° C./minute.

The following tables set forth the physical and mechanical properties of the epoxy resins of Examples 1 through 6, at room temperature. Table I shows the physical properties of the epoxy resins of Examples 1 through 3. The viscosity was not measured for Examples 1 and 2. The viscosity for Example 3, however, was determined at about 50° C. and found to be about 2900 centipoise (cps). It is important to note that the commercial epoxy resins presently available generally have viscosities greater than 10,000 cps. In contrast, Table 1 shows that the epoxy resins, Example 3, of this invention has a considerably lower viscosity, which is a processing advantage over the present commercial epoxy resins. Because this resin of this invention has such a low viscosity, it will be understood by those skilled in the art that it is suitable for more automated manufacturing processes such as, for example, resin transfer molding, reaction injection molding and pultrusion.

TABLE 1

Synthesis and Physical Properties of Diglycidylether of Benzoylresorcinol (DEBR)

| Example | 1 | 2 | 3 |
|---|---|---|---|
| Yield (%) | 96 | 99 | 97 |
| EEW | 180 | 194 | 195 |
| Total Chlorine (Wt. %) | 0.3 | 0.39 | 0.4 |
| Viscosity (at 50° C., cps) | — | — | 2900 |
| LC/GC Analysis | | | |
| Acetone (Wt. %) | 0.3 | 0.2 | 0.7 |
| Epichlorohydrin (Wt. %) | 0.06 | 0.04 | 0.1 |

To study the neat resin mechanical properties, the epoxy resins were blended with the curing agent 4-amino-phenylsulfone (DDS) at about 130°-140° C. and void-free castings were made from the molten resin blend. Summaries of the test results for the cured DEBR resins of this invention are shown in Tables 2 through 6.

Table 2 shows the mechanical properties of the cured DEBR resin of Example 1. Table 2 also shows the mechanical properties of cured Araldite ® XU MY 722 taken at 25° C. Araldite ® XU MY 722 is commercially available from Ciba-Geigy Corporation, Hawthorne, N.Y., U.S.A. Araldite ® XU MY 722 was cured with the aromatic diamine Hardener HT 976 commercially available from Ciba-Geigy Corporation. Table 2, shows that both the cured resin of Run B of this invention and the cured Araldite ® resin were cured under a similar two-step cure cycle. This two-step cure cycle subjected the resins for about two hours at about 180° C. followed by about a two hour cure at about 210° C. Table 2 shows that the epoxy resin of this invention, Run B, had a flexural strength of 26.7 ksi and a flexural modulus of 605.0 ksi as compared to the Araldite ® epoxy resin which had a flexural strength of 18.1 ksi and a flexural modulus of 579 ksi. Table 2 shows that the epoxy resin of this invention, Run B, had a tensile strength of 11.7 ksi and tensile modulus of 668.0 ksi, as compared to Araldite ® which had a tensile strength of 8.4 ksi and a tensile modulus of 605. The epoxy resin of this invention, Run B, had a dry glass transition temperature of about 171.0° C. as compared to Araldite ® which had a dry glass transition temperature of about 240° C. From these results, it will be appreciated that the epoxy resin of this invention, Run B, has improved flexural and tensile properties as compared to Araldite ®.

Although the glass transition temperature of Araldite ® is higher than that of the epoxy resin of Run B, the glass transition temperature of the epoxy resin of Run B is acceptable for most commercial resin applications. Further, another advantage of the epoxy resin of Run B is that it has a 3% moisture absorption after 48 hours of being boiled in water. In contrast, Araldite ® has a 3.7% moisture absorption.

TABLE 2
MECHANICAL PROPERTIES

| Run # | DDS Cured DEBR Resin of Example 1 A | DDS Cured DEBR Resin of Example 1 B | Cured Araldite ® XU MY 722 — |
|---|---|---|---|
| DEBR, g (From Example 1) | 100 | 100 | Araldite ®, g 100 |
| DDS, g. | 35 | 35 | *g 50 |
| Flexural Properties (Dry) | | | |
| Strength (ksi) | 32.7 | 26.7 | 18.1 |
| Modulus (ksi) | 655.4 | 605.0 | 579 |
| Elongation (%) | 6.0 | 6.5 | — |
| Flexural Properties (Wet) (After 48-hours water boil) | | | |
| Strength (ski) | — | 23.0 | — |
| Modulus (ksi) | — | 575.0 | — |
| Elongation (%) | — | 5.1 | — |
| Tensile Properties (Dry) | | | |
| Strength (ksi) | — | 11.7 | 8.4 |
| Modulus (ski) | — | 668.0 | 605 |
| Elongation (%) | — | 2.6 | 1.6 |
| Cure Cycle, Hours/°C. | | | |
| (1) | 24/120 | 2/180 | 2/180 |
| (2) | 4/175 | 2/210 | 2/210 |
| Glass Transition Temperature, °C. (TMA) | | | |
| Dry | 175.2 | 171.0 | 240 |
| Wet | — | 160.3 | — |
| Moisture Absorption (%) (After 48-hours water boil | — | 3.0 | 3.7 |
| Impact Strength (Ft-lb/in) (Notched Izod) | — | 0.5 | — |

(ksi = 1000 pounds per square inch)
(TMA = Thermal Mechanical Analysis)
(*aromatic diamine Hardener HT 976)

Table 3 shows the mechanical properties of the cured DEBR of Example 2. Table 3 shows that depending on the cure cycle, the flexural properties may be adjusted. For instance, the epoxy resin of this invention, Run C, was cured initially for about 4 hours at about 150° C. and then for about 7 hours at about 200° C. The epoxy resin of Run C had a flexural strength of 28.3 ksi, flexural modulus of 597.0 ksi and a 6.4% elongation. In contrast, Run E was cured for about one hour at about 150° C. and then cured for about 3 hours at about 225° C. Run E had a flexural strength of 24.6 ksi, flexural modulus of 623.5 ksi and a 4.7% elongation.

TABLE 3

| Mechanical Properties of DEBR Cured With DDS | | | |
|---|---|---|---|
| Run # | C | D | E |
| DEBR, g. (From Example 2) | 100 | 100 | 100 |
| DDS, g. | 36.2 | 36.2 | 36.2 |
| Flexural Properties (Dry) | | | |
| Strength (ksi) | 28.3 | 28.7 | 24.6 |
| Modulus (ksi) | 597.0 | 600.00 | 623.5 |
| Elongation (%) | 6.4 | 6.9 | 4.7 |
| Cure Cycle, Hours/°C. | | | |

TABLE 3-continued

| Mechanical Properties of DEBR Cured With DDS | | | |
|---|---|---|---|
| Run # | C | D | E |
| (1) | 4/150 | 2/150 | 1/150 |
| (2) | 7/200 | 4/200 | 3/225 |
| Glass Transition Temperature, °C. (TMA) (Dry) | 166 | 164.5 | 173.4 |
| Moisture Absorption (%) (After 48-hours water boil) | — | 3.1 | 3.0 |
| Impact Strength (Ft-lb/in) (Notched Izod) | — | 0.38 | 0.4 |

Table 4 shows the mechanical properties of cured DEBR of Example 3. Table 4 shows that different cure cycles wee used for Runs F and G. Accordingly, the properties of flexural strength, flexural modulus and % elongation vary for Runs F and G.

TABLE 4

| Mechanical Properties of DEBR Cured with DDS | | |
|---|---|---|
| Run # | F | G |
| DEBR, g. (From Example 3) | 100 | 100 |
| DDS, g. | 36.2 | 36.2 |
| Flexural Properties (Dry) | | |
| Strength (ksi) | 25.2 | 27.0 |
| Modulus (ksi) | 634.8 | 627.3 |
| Elongation (%) | 5.4 | 6.2 |
| Flexural Properties (Wet (After 48-hours water boil) | | |
| Strength (ksi) | 20.5 | 21.0 |
| Modulus (ksi) | 588.1 | 591.4 |
| Elongation (%) | 4.1 | 4.3 |
| Cure Cycle, Hours/°C. | | |
| (1) | 2/180 | 2/150 |
| (2) | 2/210 | 4/200 |

Table 5 shows the mechanical properties of diglycidylether of styrylresorcinol (DGES) of Example 4 that has been cured with DDS. Table 5 shows that the epoxy resin of Run H had a very high flexural modulus of 686.2 ksi but had a low glass transition temperature of 128.8° C.

TABLE 5

| Mechanical Properties of DGESR Cured with DDS | |
|---|---|
| Run # | H |
| DGESR, g. (From Example 4) | 100 |
| DDS, g. | 27.5 |
| Flexural Properties (Dry) | |
| Strength (ksi) | 18.7 |
| Modulus (ksi) | 686.2 |
| Elongation (%) | 2.8 |
| Cure Cycle, Hours/°C. | |
| (1) | 23/120 |
| (2) | 4/175 |
| Glass Transition Temperature, °C. (TMA) Dry | 128.8 |

Table 6 shows the mechanical properties of diglycidylether of alpha-methylstyrylresorcinol (DGEMSR) of Example 6 that has been cured with DDS. Table 6 shows that the epoxy resin of Run I had an acceptable glass transition temperature of 164.8° C. and had acceptable flexural properties. The epoxy resin of Run I had a 2% moisture absorption after 48 hours of water boil. It will be appreciated, therefore, that the epoxy resin of Run I has a very low moisture absorption ability. This property is particularly advantageous for a resin employed in an environment having a high humidity level.

TABLE 6

| Mechanical Properties of DGEMSR Cured with DDS | |
|---|---|
| Run # | I |
| DGEMSR, g. (From Example 6) | 100 |
| DDS, g. | 20.5 |
| Flexural Properties (Dry) | |
| Strength (ksi) | 12.8 |
| Modulus (ksi) | 541.1 |
| Elongation (%) | 2.4 |
| Flexural Properties (Wet) | |
| (After 48-hours water boil) | |
| Strength (ksi) | 7.6 |
| Modulus (ksi) | 555.0 |
| Elongation (%) | 1.1 |
| Cure Cycle, Hours/°C. | |
| (1) | 2/120 |
| (2) | 4/200 |
| Glass Transition Temperature, °C. (TMA) Dry | 164.8 |
| Moisture Absorption (%) (After 48-hours water boil) | 2.0 |
| Impact Strength (Ft-lb/in) (Notched Izod) | 0.48 |

Example 7 sets forth the preparation of an epoxy resin of this invention that may be made from 1,3-bis[2,4-dihydroxyphenyl)-alpha-methyl-ethyl] benzene. The resulting epoxy resin of Example 7 was cured for about 2 hours at about 150° C. and then for about 4 hours at about 200° C. Thermal mechanical analysis measurements showed a glass transition temperature for this epoxy resin of 244.7° C. Accordingly, it will be appreciated that the epoxy resin of Example 7 had a glass transition temperature greater than the glass transition temperature of the epoxy resins of Examples 1 through 6.

The hereinbefore data clearly demonstrates that the epoxy resins of this invention have improved mechanical and physical properties over the presently commercially available epoxy resins.

Whereas particular embodiments of this invention have been described above for purposes of illustration, it will be evident to those persons skilled in the art that numerous variations of the details of the present invention may be made without departing from the invention as defined in the appended claims.

What is claimed is:

1. A curable epoxy resin having the general structural formula (V)

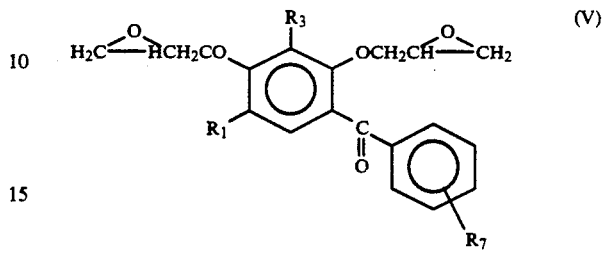

wherein $R_1$ and $R_3$ may be the same or different and selected from the group consisting of (a) hydrogen, (b) the general structural formula (VI)

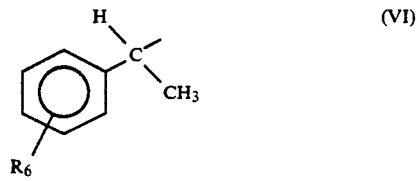

and (c) an allyl group, and wherein $R_6$ and $R_7$ may be the same or different and selected from the group consisting of hydrogen and an alkyl group having 1 to about 4 carbon atoms.

2. The curable epoxy resin of claim 1, having the general structural formula (V), wherein said epoxy resin is characterized by being nontoxic to human beings.

3. The curable epoxy resin of claim 1, wherein $R_1$, $R_3$, and $R_7$ are hydrogen.